(12) United States Patent
Shulman

(10) Patent No.: US 10,265,214 B2
(45) Date of Patent: Apr. 23, 2019

(54) EYE DROP APPLICATOR

(71) Applicant: Magic Touch Eye, Inc., New York, NY (US)

(72) Inventor: Julius Shulman, New York, NY (US)

(73) Assignee: Magic Touch Eye, Inc., New York, NY (US)

( * ) Notice: Subject to any disclaimer, the term of this patent is extended or adjusted under 35 U.S.C. 154(b) by 296 days.

(21) Appl. No.: 15/244,750

(22) Filed: Aug. 23, 2016

(65) Prior Publication Data

US 2017/0056241 A1    Mar. 2, 2017

Related U.S. Application Data

(60) Provisional application No. 62/208,940, filed on Aug. 24, 2015.

(51) Int. Cl.
*A61F 9/00* (2006.01)
*A61M 35/00* (2006.01)

(52) U.S. Cl.
CPC ......... *A61F 9/0008* (2013.01); *A61M 35/003* (2013.01); *A61F 9/0061* (2013.01)

(58) Field of Classification Search
CPC ...... A61F 9/0008; A61F 9/0061; D05B 91/04
See application file for complete search history.

(56) References Cited

U.S. PATENT DOCUMENTS

| | | | |
|---|---|---|---|
| 113,601 A * | 4/1871 | Wansleben | D05B 91/04 223/101 |
| 1,336,109 A | 4/1920 | Tullinger | |
| 20,191,071 | 10/1935 | Carr | |
| 2,589,499 A * | 3/1952 | Lake | D05B 91/04 223/101 |
| 2,673,661 A | 3/1954 | Barton | |
| 3,016,898 A | 1/1962 | Erwin | |
| 3,958,528 A | 5/1976 | Hill | |
| 4,085,750 A | 4/1978 | Bosshold | |
| D248,448 S | 7/1978 | Mcclure et al. | |
| 4,761,381 A | 8/1988 | Blatt et al. | |
| 4,834,728 A | 5/1989 | McKenna | |
| 4,913,682 A | 4/1990 | Shabo | |

(Continued)

FOREIGN PATENT DOCUMENTS

| DE | 29711373 U1 | 9/1997 |
|---|---|---|
| WO | 2014/055676 A1 | 4/2014 |
| WO | 2014/111802 A1 | 7/2014 |

OTHER PUBLICATIONS

Notice of Allowance, Design U.S. Appl. No. 29/564,315, dated Oct. 4, 2016, 10 pages.
Notice of Allowance, Design U.S. Appl. No. 29/545,356, dated Oct. 31, 2016, 11 pages.
The Newest Unique Designed BPA Free Silicone Travel Bottle/Names of Eye Drops http://www.alibaba.com/product-detail/The-Newest-Unique-Designed-BPA-Free_716366566.html; believed to be available as early as Jun. 16, 2015.

(Continued)

*Primary Examiner* — Adam Marcetich
*Assistant Examiner* — Jessica R Arble
(74) *Attorney, Agent, or Firm* — Kilpatrick Townsend & Stockton LLP

(57) ABSTRACT

An eye drop applicator includes a main body with a lower portion and an upper portion having a cavity configured to retain a predetermined amount of medication. The lower portion may include an opening configured to snuggly receive a user's finger and/or a top of a medication bottle. The eye drop applicator may also include a removable cap configured to attach to the upper portion of the main body to cover the cavity.

24 Claims, 6 Drawing Sheets

(56) References Cited

U.S. PATENT DOCUMENTS

| | | | |
|---|---|---|---|
| 4,960,407 A | 10/1990 | Cope | |
| 4,968,310 A | 11/1990 | Menchel et al. | |
| 5,007,905 A | 4/1991 | Bauer | |
| 5,040,706 A | 8/1991 | Davis et al. | |
| 5,246,145 A | 9/1993 | Leoncavallo et al. | |
| 5,387,202 A | 2/1995 | Baron | |
| 5,611,464 A | 3/1997 | Tsao et al. | |
| 5,756,050 A | 5/1998 | Ershow et al. | |
| 5,902,292 A | 5/1999 | Feldman | |
| 6,051,190 A | 4/2000 | Birch et al. | |
| 6,159,189 A | 12/2000 | Finnemore et al. | |
| 6,197,008 B1 | 3/2001 | Hagele et al. | |
| 6,331,085 B1 | 12/2001 | Schrepf et al. | |
| 6,401,915 B1* | 6/2002 | Faxe | A45C 11/005 206/210 |
| 6,632,202 B1 | 10/2003 | Hagele et al. | |
| 6,913,406 B1 | 7/2005 | Nocerino | |
| 7,178,703 B2 | 2/2007 | Spada et al. | |
| 7,476,043 B1 | 1/2009 | Rivas | |
| 7,527,613 B2 | 5/2009 | Gaynes | |
| D597,213 S | 7/2009 | Barnett | |
| 7,678,089 B2 | 3/2010 | Py et al. | |
| 7,758,553 B2 | 7/2010 | Poisson et al. | |
| D676,126 S | 2/2013 | Hair | |
| 8,444,610 B2 | 5/2013 | Grevin et al. | |
| 8,679,078 B2 | 3/2014 | Leahy et al. | |
| D736,906 S | 8/2015 | Schultz | |
| D743,019 S | 11/2015 | Schultz | |
| D763,078 S | 8/2016 | Roy | |
| 2006/0129113 A1 | 6/2006 | Merrick | |
| 2006/0198692 A1 | 9/2006 | Petit | |
| 2007/0199831 A1* | 8/2007 | Tokarski | A45C 11/005 206/5.1 |
| 2007/0287123 A1 | 12/2007 | Swift et al. | |
| 2009/0105749 A1 | 4/2009 | de Juan et al. | |
| 2010/0234319 A1 | 9/2010 | Yu | |
| 2011/0306942 A1 | 12/2011 | Thorpe | |
| 2013/0220851 A1* | 8/2013 | Priebe | A45C 11/005 206/234 |
| 2014/0094759 A1 | 4/2014 | Mansfield | |
| 2014/0350492 A1 | 11/2014 | Rojas Escalante et al. | |

OTHER PUBLICATIONS

5pcs Mini Facial Eye Silicone Massage Cup Diameter 6 Mm Cupping Vacuum Chinese http://www.aliexpress.com/item/5pcs-MINI-FACIAL-EYE-SILICONE-MASSAGE-CUP-DIAMETER-6-MM-CUPPING-VACUUM-CHINESE/2021900579.html: believed to be available as early as Jun. 16, 2015.

Bradley Fixtures Opti-Aid™ Plus Personal Eyewash Station https://www.fishersci.com/shop/products/bradley-fixtures-opti-aid-plus-personal-eyewash-station/p-3526554; believed to be available as early as Jun. 16, 2015.

https://web.archive.org/web/20110220003150/http://eyepodmagic.com Feb. 20, 2011.

http://www.prnewswire.com/news-releases/inventor-discovers-a-new-way-of-inserting-contact-lens-in-1-second—finger-free-79397202.html.; Dec. 16, 2009.

http://www.news-medical.net/news/20091211/Hot-Ideas-World-creates-Eye-POD-Eye-Care-Kit.aspx ; Dec. 11, 2009.

"Lab Supplies." MidAtlantic Ortho. MidAtlantic Ortho, Aug. 2, 2009. Web. Oct. 1, 2013, http://www.midatlanticortho.com/lab_supplies.php.

Tiwari, Rajkiran, and D.R. Paul. "Polypropylene-elastomer (TPO) nanocomposites." Elsevier: Polymer. 52.21 (2011): 4955-4969. Web. Oct. 3, 2013. http://www.sciencedirect.com/science/article/pii/S0032386111006859#.

Shmulinson, Michal, Mercedes Galan-Fereres, et al. "Formation of Elastomeric Polypropylene Promoted by Racemic Acteylacetonate Group 4 Complexes." Organometallics. 19 (1999): 1208-1210. Web. Oct. 3, 2013. http://pubs.acs.org/doi/pdf/10.1021/om9908985.

"Vistamaxx propylene-based elastomer." ExxonMobil Chemical. N.p., Jan. 29, 2010. Web. Oct. 3, 2013. http://www.exxonmobilchemcial.com/Chem-English/brands/vistamaxx-propylene-based-elastomers.aspx?in=productsservices.

Non-Final Office Action, Design U.S. Appl. No. 29/545,356, dated Sep. 1, 2016, 8 pages.

Notice of Allowance, Design U.S. Appl. No. 29/564,315, dated Sep. 2, 2016, 6 pages.

Office Action, Indian Design Application No. 283265, dated Aug. 9, 2016, 2 pages.

\* cited by examiner

EYE DROP APPLICATOR

CROSS REFERENCE TO RELATED APPLICATION

This application is related to and claims priority benefits from U.S. Provisional Application Ser. No. 62/208,940 ("the '940 application"), filed on Aug. 24, 2015, entitled EYE DROP APPLICATOR. The '940 application is hereby incorporated in its entirety by this reference.

FIELD OF THE INVENTION

This invention relates to devices and methods for applying eye drops.

BACKGROUND

Eye drops are a common treatment for numerous eye ailments including both prescription and non-prescription drops. However, people using conventional eye drop application techniques are often not successful in applying a drop into the conjunctival sac of the eye.

A product is needed to facilitate successful applications of eye drops to ensure successful treatment of eye ailments and prevent wasting medication.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

Disclosed is an eye drop applicator that includes a main body comprising a lower portion and an upper portion attached to the top of the lower portion such that the upper portion includes a cavity for retaining a predetermined amount of medication, and a removable cap configured to cover the cavity. The lower portion may include an opening configured to receive a user's finger.

BRIEF DESCRIPTION OF THE DRAWINGS

Illustrative embodiments of the present invention are described in detail below with reference to the following drawing figures.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

The figures illustrate an exemplary eye drop applicator 100 that facilitates measurement and accurate, effective administration of a medication, such as eye drops or any type of liquid medication. As described in more detail below, the eye drop applicator 100 can securely hold an appropriate amount of medication and facilitates a natural and effective application/delivery of medication.

Figure 1:
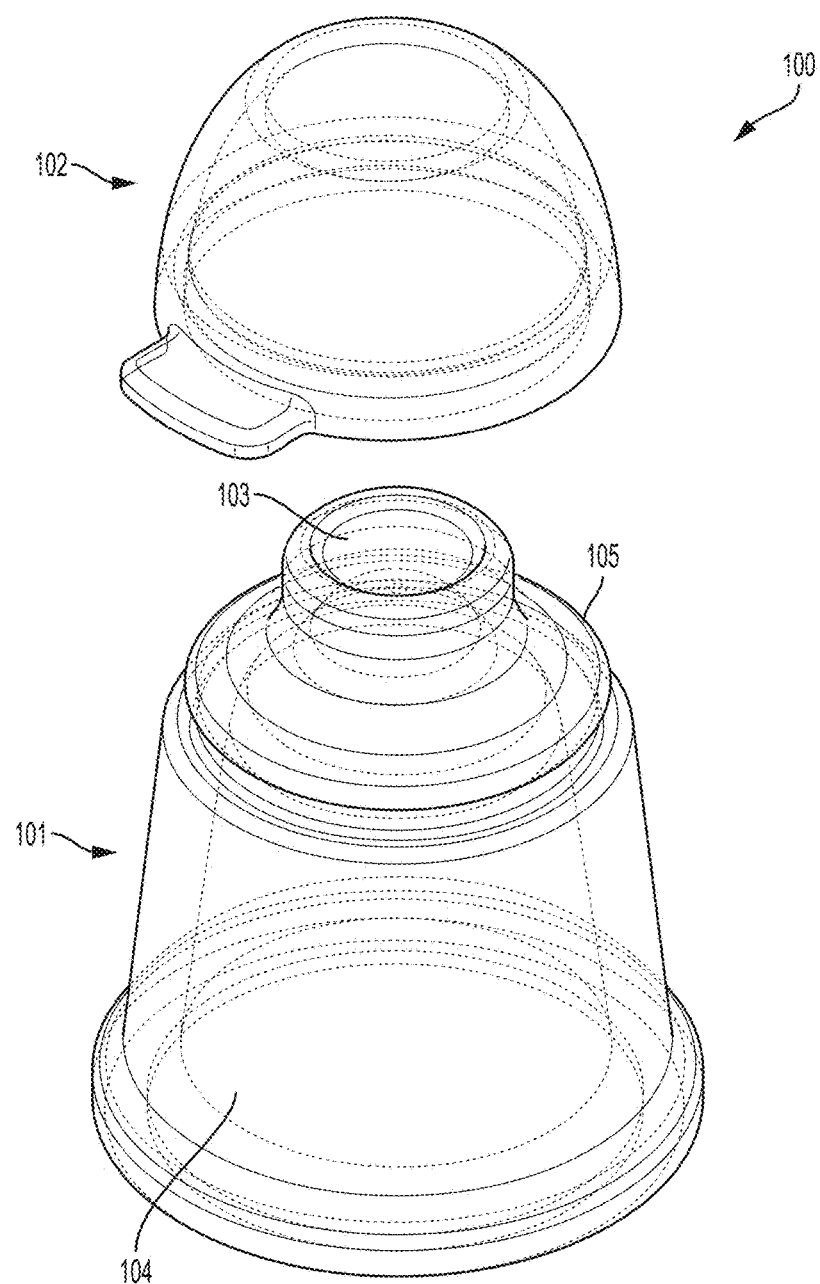
FIG. 1 is a perspective view of an eye drop applicator according to one example of this invention, shown with the cap in a detached position.
Figure 2A:
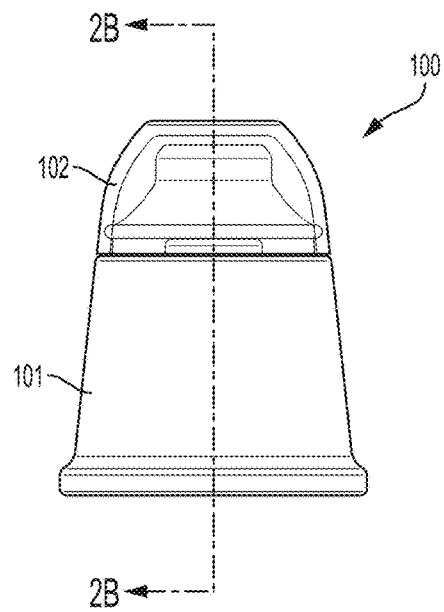
FIG. 2A is a front view of the eye drop applicator depicted in FIG. 1.
Figure 2B:
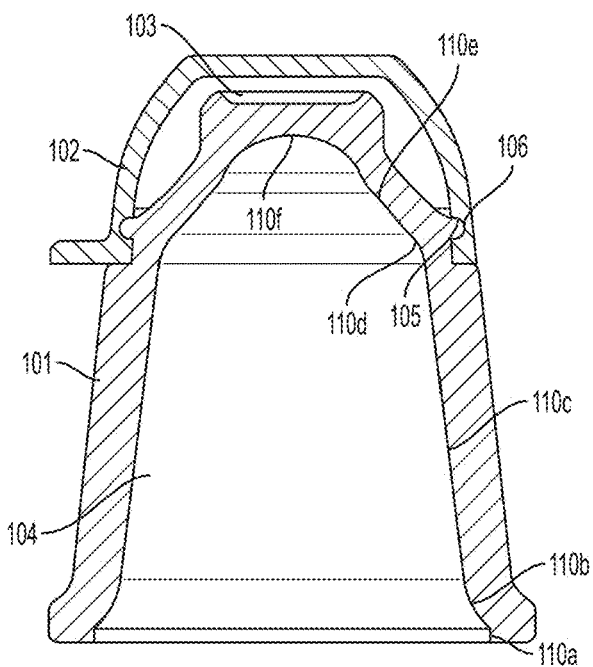
FIG. 2B is a cross-sectional view of the eye drop applicator of FIG. 1A, taken along line 2B-2B in FIG. 2A.
Figures 3A, 3B:
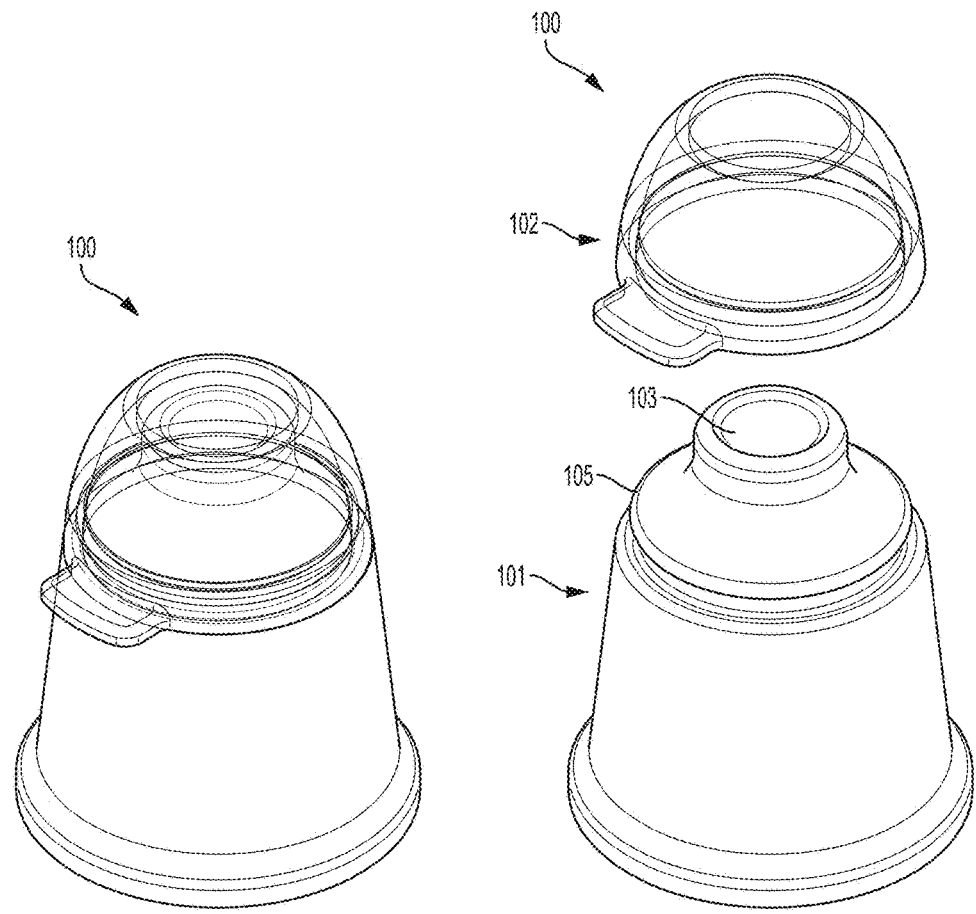
FIG. 3A is a perspective view of the eye drop applicator depicted in FIG. 1, shown with the cap in an attached position.
FIG. 3B is a perspective view of the eye drop applicator depicted in FIG. 1, shown with the cap in the detached position.
Figure 5:
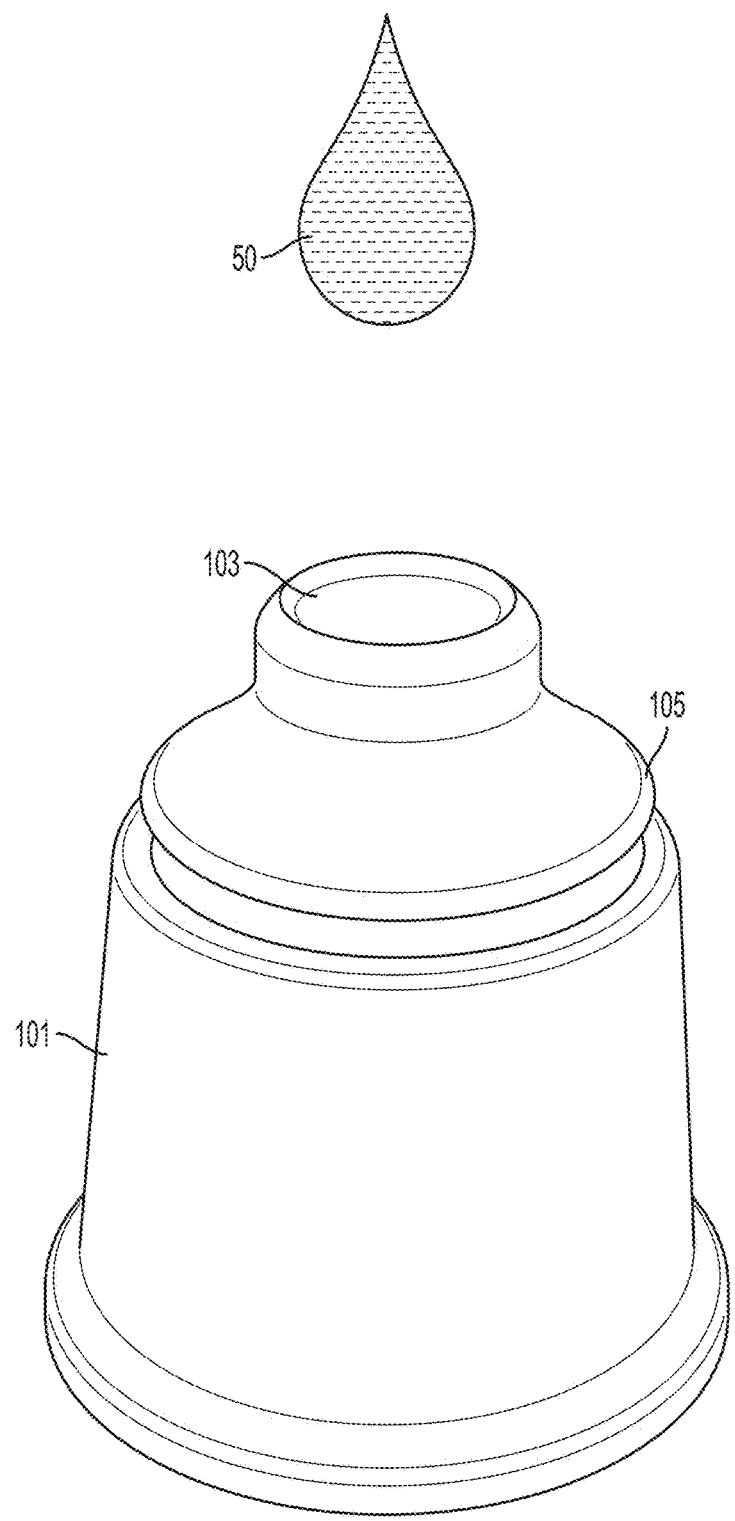
FIG. 5 is a perspective view of the eye drop applicator depicted in FIG. 1, shown relative to an eye drop.

As illustrated in FIGS. 1-2B, the eye drop applicator 100 includes a main body 101 and a cap 102 configured to attach to an upper portion of the main body 101. The upper portion of the main body 101 includes a cavity 103 configured to hold an appropriate amount of medication 50 (see FIG. 5). In some examples, the appropriate amount is approximately 1-5 drops. In some examples, the appropriate amount is approximately 1-2 drops or approximately 1 drop. The cavity 103 may be a depression, may be dish-shaped, may be bowl-shaped, or may be any other appropriate shape configured to hold an appropriate amount of medication by surface tension or otherwise, as described below. The lower portion of the main body 101 may include an opening 104 that is configured to snuggly receive a user's finger 1 so that the eye drop applicator 100 is secured to a user's finger (see FIG. 6).

As shown in FIGS. 1-3B, the main body 101 may include an engagement member 105 configured to attach and/or secure the cap 102 onto the main body 101. In some examples, the engagement member 105 is an annual protrusion that extends around the circumference of the main body 101. The cap 102 includes one or more features adjacent its lower edge that are complimentary to the engagement member 105 of the main body 101. In some examples, the one or more features of the cap are a channel, a groove, a notch and/or a protrusion that interfaces with the engagement member 105. To allow a user to attach the cap 102 onto the main body 101, the engagement member 105 may be at least somewhat flexible and/or the cap 102 may be at least somewhat flexible. As shown in FIG. 2B, when the cap 102 engages the main body 101, the engagement member 105 of the main body 101 engages a channel 106 of the cap 102 to snap the cap 102 onto the main body 101. The cap 102 protects the cavity 103 from contamination, physical damage, or any other damage. For example, the use of cap 102 may reduce the need for frequent sterilization of the cavity 103.

To accommodate various shapes of users' fingers, the opening 104 of the main body 101 may include a variable diameter D along a height H of the main body 101. As shown in the cross-section view in FIG. 2B, the opening 104 may include a maximum diameter at a first portion 110*a* near the bottom of the main body 101. The first portion 110*a* extends from a bottom of the main body 101 up to a height $H_1$ and has a constant diameter along height $H_1$. In other words, the opening 104 is cylindrical at first portion 110*a* along section $H_1$. As shown in FIG. 2B, above first portion 110*a*, the inner diameter of the opening 104 continually decreases. Above the first portion 110*a*, there is a second portion 110*b* that extends along a section $H_2$ and includes a decreasing diameter such that the inner surface of the opening 104 curves and forms a convex shape along section or height $H_2$. Above the second portion 110*b*, there is a third portion 110*c* extending along height $H_3$ with a diameter that is smaller than the diameters of the first and second portions. In some cases, the decrease in diameter along third portion 110*c* is linear. In some cases, the inner surface of the opening 104 includes a straight taper at portion 110*c* along section or height $H_3$. A fourth portion 110*d* is located above the third portion 110*c* that extends along height $H_4$. The fourth portion 110*d* includes a decreasing diameter such that an inner surface of the opening 104 curves and forms a concave shape along section or height $H_4$. Above the fourth portion 110*d*, there is a fifth portion 110*e* extending along section or height $H_5$. In some cases, the decrease in diameter along at least some of the fifth portion 110*e* is linear. As such, the opening 104 may include two areas—along portions 110*c* and 110*e*—with a straight taper. Above the fifth portion 110*e*, the opening 104 includes a dome or rounded portion 110*f* along section or height $H_6$.

Figure 4:
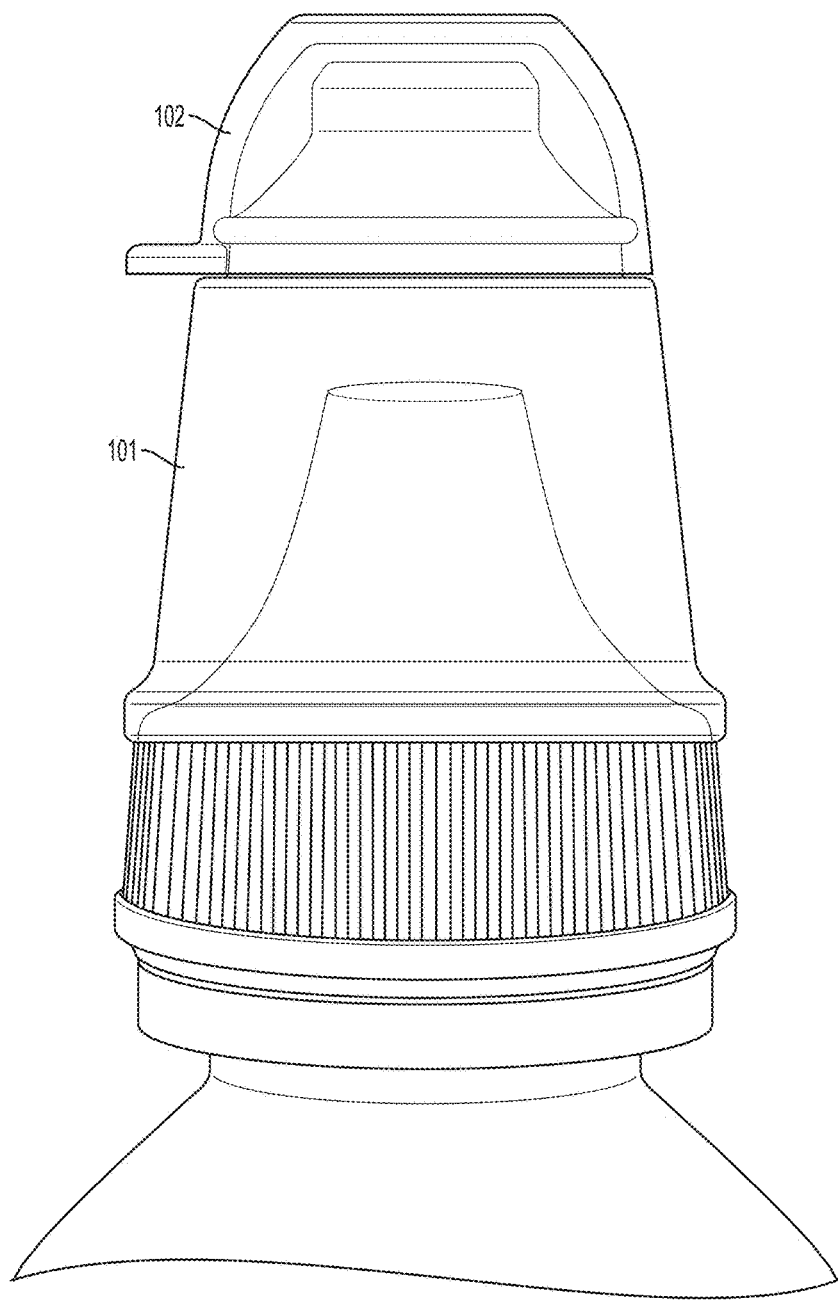
FIG. 4 is a front view of the eye drop applicator depicted in FIG. 1 coupled to a medication bottle.

As shown in FIG. 4, in addition to fitting on a finger 1 of a user, the opening 104 of the eye drop applicator may be configured to attach to the top of an eye drop bottle.

Figure 6:
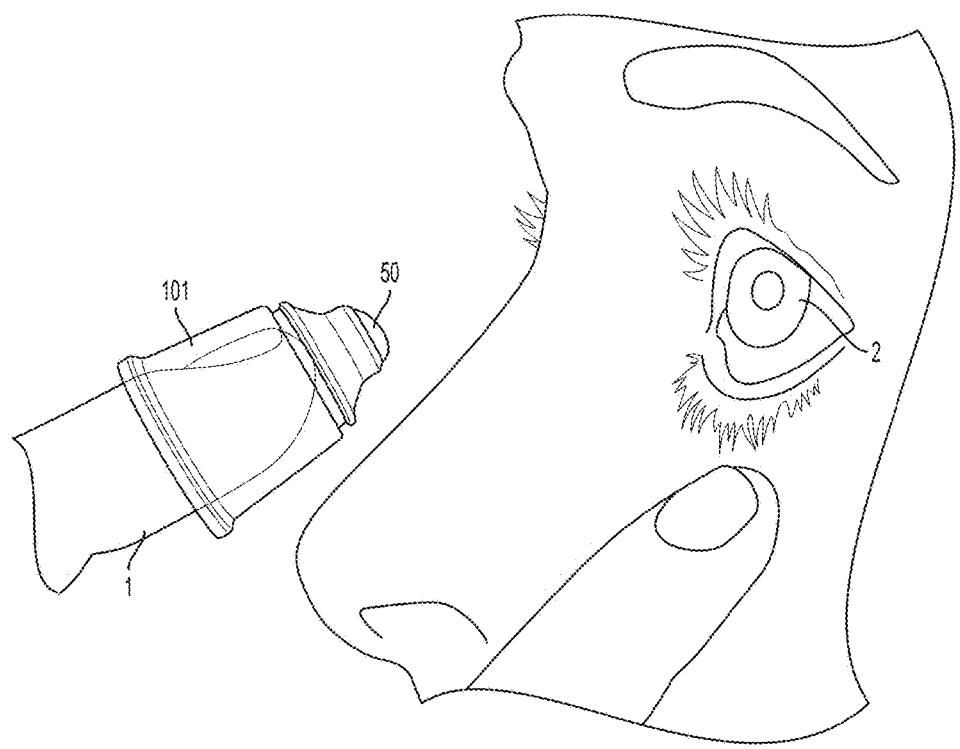
FIG. 6 is a side view of the eye drop applicator depicted in FIG. 1, positioned relative to a user's eye.

After the medication 50 is placed in cavity 103 (see FIG. 5), the eye drop applicator 100 securely retains the medication within the cavity 103. For example, even when the eye drop applicator 100 is tilted (as shown in FIG. 6), the medication 50 remains secure in the cavity 103. This is accomplished by maintaining sufficient surface tension in the medication based on the geometry of the cavity 103 and/or the material properties of the upper portion of the eye drop applicator 100.

In some examples, the cavity 103 is constructed from medical-grade silicone or any other appropriate material. If desired, the entire upper portion of the eye drop applicator 100 or even the entire eye drop applicator 100 may be constructed from medical-grade silicone or any other appropriate material. To reduce the amount of medical-grade silicone (or other appropriate material) necessary, the lower portion of the eye drop applicator 100 (or all of the eye drop applicator 100 other than the cavity 103) may be constructed from other materials such as rigid plastic, soft plastic, polycarbonate, polyethylene, polyethylene terephthalate, acrylonitrile butadiene styrene, or any other suitable material.

To provide an antimicrobial effect, a surface of one or more components of the eye drop applicator 100 may be treated with a coating either during the manufacturing process or after the manufacturing process is complete. In some examples, the coating may include silver ions and/or particles of a thermoplastic polymer containing an organic biocide where the coating is electrostatically sprayed onto the one or more surfaces (or formed as part of the surfaces during the manufacturing process). In addition, the coating may be any known type of antimicrobial coating. The coating may be applied to the inner surface of the cap 102, to the surface of cavity 103, and/or any other surface of the eye drop applicator 100.

To apply the medication, the eye drop applicator 100 is raised to the recipient's eye 2 similar to the motion for inserting a contact lens such that the portion of the medication 50 protruding from the cavity 103 touches the eye (without touching the eye drop applicator 100 to the eye 2). In some cases, the eye drop applicator 100 may touch the eye 2 and, in some instances, may touch the user's lower eyelid. The contact with the surface of the user's eye 2 disrupts the surface tension of medication 50. After breaking the surface tension, the medication flows from the cavity 103 to the user's eye via gravity or capillary action or a combination of both gravity and capillary action.

Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

That which is claimed is:

1. An eye drop applicator comprising:
   a main body comprising:
   (1) a lower portion with an opening configured to receive a user's finger, wherein the opening comprises a variable diameter that changes along a height of the main body; and
   (2) an upper portion, wherein the upper portion comprises a cavity configured to retain a predetermined amount of liquid medication; and
   wherein a majority of a bottom surface of the cavity comprises a continuous flat surface.

2. The eye drop applicator of claim 1, wherein the liquid medication is eye medication.

3. The eye drop applicator of claim 1, wherein the predetermined amount is approximately 1-2 drops.

4. The eye drop applicator of claim 1, wherein the cavity is configured to retain the liquid medication using surface tension.

5. The eye drop applicator of claim 1, wherein the opening comprises a maximum diameter adjacent a lower edge of the main body.

6. The eye drop applicator of claim 1, wherein the opening comprises a first portion with a constant diameter along a section of the height of the main body such that an inner surface of the opening forms a cylindrical shape along the first portion.

7. The eye drop applicator of claim 1, wherein the opening comprises a fourth portion with a decreasing diameter along a section of the height of the main body such that an inner surface of the opening curves and forms a concave shape along the fourth portion.

8. The eye drop applicator of claim 1, wherein the opening comprises a third portion with a linearly decreasing diameter along a section of the height of the main body such that an inner surface of the opening includes a straight taper along the third portion.

9. The eye drop applicator of claim 1, wherein the opening comprises a second portion with a decreasing diameter along a section of the height of the main body such that an inner surface of the opening curves and forms a convex shape along the second portion.

10. The eye drop applicator of claim 8, further comprising a fifth portion comprising a linearly decreasing diameter.

11. The eye drop applicator of claim 1, wherein the opening comprises a top portion that is dome shaped.

12. The eye drop applicator of claim 1, further comprising a removable and replaceable cap configured to cover the cavity, wherein the main body comprises an engagement member configured to engage with one or more features of the removable and replaceable cap to secure the removable and replaceable cap.

13. The eye drop applicator of claim 12, wherein the engagement member comprises an annular protrusion and the one or more features comprises a channel.

14. An eye drop applicator comprising:
a main body comprising a cavity configured to retain a predetermined amount of medication and an opening configured to receive a user's finger;
wherein:
the cavity comprises a continuous flat surface that is recessed relative to an uppermost portion of the main body; and
the opening comprises a diameter that decreases along a height of the main body toward a top of the main body.

15. The eye drop applicator of claim 14, wherein the cavity is configured to retain the medication using surface tension.

16. The eye drop applicator of claim 14, wherein the opening comprises a maximum diameter adjacent a lower edge of the main body.

17. The eye drop applicator of claim 14, wherein the opening comprises a first portion with a constant diameter along a section of the height of the main body such that an inner surface of the opening forms a cylindrical shape along the first portion.

18. The eye drop applicator of claim 14, wherein the opening comprises a third portion with a linearly decreasing diameter along a section of the height of the main body such that an inner surface of the opening includes a straight taper along the third portion.

19. The eye drop applicator of claim 14, wherein the opening comprises a second portion with a decreasing diameter along a section of the height of the main body such that an inner surface of the opening curves and forms a convex shape along the second portion.

20. The eye drop applicator of claim 14, further comprising a removable and replaceable cap configured to cover the cavity, wherein the main body comprises an engagement member that engages with one or more features of the removable cap to secure the removable and replaceable cap.

21. The eye drop applicator of claim 20, wherein the engagement member comprises an annular protrusion and the one or more features comprises a channel.

22. The eye drop applicator of claim 1, wherein the main body comprises a rim disposed at a perimeter of the cavity such that the rim extends in a direction that is approximately perpendicular to the flat surface.

23. The eye drop applicator of claim 1, wherein the opening comprises:
a first portion with a constant diameter along a section of the height of the main body such that an inner surface of the opening forms a cylindrical shape along the first portion;
a second curved portion with a decreasing diameter along a section of the height of the main body such that the inner surface of the opening curves and forms a concave shape along the second curved portion; and
a third portion with a linearly decreasing diameter along a section of the height of the main body such that the inner surface of the opening includes a straight taper along the third portion.

24. The eye drop applicator of claim 23, wherein the inner surface of the opening transitions directly from the first portion to the second curved portion and from the second curved portion to the third portion.

* * * * *